US009226667B2

(12) United States Patent
Grotov

(10) Patent No.: US 9,226,667 B2
(45) Date of Patent: Jan. 5, 2016

(54) BLOOD PRESSURE MONITOR CALIBRATION

(76) Inventor: Yury Grotov, Basseterre (KN)

( * ) Notice: Subject to any disclaimer, the term of this patent is extended or adjusted under 35 U.S.C. 154(b) by 400 days.

(21) Appl. No.: 13/811,821

(22) PCT Filed: Jul. 25, 2011

(86) PCT No.: PCT/GB2011/051411
§ 371 (c)(1),
(2), (4) Date: Jan. 28, 2013

(87) PCT Pub. No.: WO2012/010909
PCT Pub. Date: Jan. 26, 2012

(65) Prior Publication Data
US 2013/0125613 A1  May 23, 2013

(30) Foreign Application Priority Data

Jul. 23, 2010 (GB) .................................. 1012337.0

(51) Int. Cl.
*A61B 5/021* (2006.01)
*A61B 5/022* (2006.01)
*A61B 5/0225* (2006.01)
(Continued)

(52) U.S. Cl.
CPC .............. *A61B 5/021* (2013.01); *A61B 5/0225* (2013.01); *A61B 5/02225* (2013.01); *A61B 5/6824* (2013.01); *G01L 27/005* (2013.01); *A61B 2560/0223* (2013.01); *A61B 2560/0252* (2013.01)

(58) Field of Classification Search
None
See application file for complete search history.

(56) References Cited

U.S. PATENT DOCUMENTS 4,269,058 A   5/1981 Richman
4,658,829 A * 4/1987 Wallace ........................ 600/488
(Continued)

FOREIGN PATENT DOCUMENTS

JP       07178065 A    7/1995
JP     2009153843 A    7/2009

OTHER PUBLICATIONS

International Search Report and the Written Opinion of the International Searching Authority relating to International Application No. PCT/GB2011/051441, dated Dec. 27, 2011.
(Continued)

*Primary Examiner* — Andre Allen

(57) ABSTRACT

A blood pressure monitor, particularly of the type having an inflatable cuff communicating with a pressure sensor and suitable for home use, may be calibrated by applying a sealed canister containing gas at a known pressure to a port so as to apply the known pressure to the pressure sensor, and comparing a pressure signal from the pressure sensor with the known pressure so as to determine a calibration error of the sensor and/or adjust the calibration of the sensor, e.g. by electronically adjusting the sensor. Several canisters may be used to calibrate the sensor across a range of pressures, each canister having a different known pressure. Each canister is preferably ruptured when attached to the port and is not re-usable, and may comprise an identifier such as an electronically readable identifier which is stored in a memory in association with the value of the known pressure within the canister. Temperature sensing means may be provided whereby the pressure reading is adjusted to compensate for temperature, e.g. of the gas released from the canister. The monitor may comprise means for sensing mechanical shock and alerting a user or remote monitoring personnel to provide an indication that recalibration is required.

16 Claims, 1 Drawing Sheet

(51) Int. Cl.
*A61B 5/00* (2006.01)
*G01L 27/00* (2006.01)

(56) References Cited

U.S. PATENT DOCUMENTS

| | | | |
|---|---|---|---|
| 5,711,302 A * | 1/1998 | Lampropoulos et al. | 600/485 |
| 6,984,212 B1 | 1/2006 | Yang | |
| 2002/0198458 A1 | 12/2002 | Tripp et al. | |
| 2005/0131307 A1 | 6/2005 | Ruiter et al. | |
| 2008/0039731 A1 * | 2/2008 | McCombie et al. | 600/485 |
| 2008/0077021 A1 | 3/2008 | Ferber et al. | |
| 2009/0138207 A1 | 5/2009 | Cosentino et al. | |
| 2013/0125613 A1 * | 5/2013 | Grotov | 73/1.63 |
| 2013/0172691 A1 * | 7/2013 | Tran | 600/301 |
| 2014/0276145 A1 * | 9/2014 | Banet et al. | 600/490 |
| 2015/0099941 A1 * | 4/2015 | Tran | 600/300 |

OTHER PUBLICATIONS

UK Search Report under Section 17 relating to Application No. GB1012337.0, dated Mar. 15, 2011.

* cited by examiner

BLOOD PRESSURE MONITOR CALIBRATION

The present invention relates to blood pressure monitor calibration, in particular the calibration of a blood pressure monitor using a known pressure.

Cardiovascular disease (CVD) is responsible for one third of global deaths and is a leading and increasing contributor to the global disease burden. Hypertension is already a highly prevalent risk factor for CVD throughout the industrialised world, and is becoming an increasingly common health problem in many developing countries, particularly in urban societies.

The accurate measurement of blood pressure is the sine qua non for successful management of hypertension. Blood pressure is usually measured using a sphygmomanometer or blood pressure monitor. One of the main factors influencing the accuracy of measurement of blood pressure by a blood pressure monitor is the sensor of pressure, the signal from which is processed and transformed into a measure of blood pressure (for example, in mmHg), which later is used for diagnostics and treatment of most CVD. But with time, as well as under influence of different external factors such as shock to or dropping of the device, temperature changes, ageing of the components, etc, the accuracy of the sensor changes, which causes errors in measurement. One of the main problems is often the dropping of the blood pressure monitor, as the main users of blood pressure monitors are elderly and sick people. That is why blood pressure measurement devices, whether aneroid, mercury, or electronic, and including all home blood pressure measurement devices, must be checked regularly for accuracy.

Calibration is performed by attaching the blood pressure monitor to a highly accurate specialised compressor and checking that the pressure displayed by the blood pressure monitor matches that being generated by the compressor. These compressors are usually maintained by the manufacturers or by specialist companies. The blood pressure monitors are sent away to the companies for calibration. This is expensive and inconvenient; further, the blood pressure monitor may be dropped or damaged during transit back from the calibration company, so that the blood pressure monitor is again inaccurate.

Due to these problems, although all consumer blood pressure monitors are calibrated during manufacture, many are never calibrated again. This of course negatively influences the quality of diagnostics and treatment of millions of users of blood pressure monitors.

An object of the present invention is to enable blood pressure monitors to be calibrated in a cheap and convenient manner, particularly by the users thereof.

Accordingly in its various aspects the invention provides a method, a system and a blood pressure monitor as defined in the claims.

According to a first embodiment of the invention there is provided a method for checking or adjusting the calibration of a blood pressure monitor, the blood pressure monitor including a pressure sensing means, comprising the step of taking at least one sealed canister containing a known pressure, connecting the canister in fluid communication with the pressure sensing means so as to apply the known pressure to the pressure sensing means, obtaining a reading from the pressure sensing means while the canister is in fluid communication therewith, and comparing the reading obtained from the pressure sensing means with an expected reading so as to check or calibrate the blood pressure monitor.

According to a further embodiment of the present invention, there is provided a system comprising: a blood pressure monitor including a pressure sensor and at least one port in fluid communication with the pressure sensor; and a canister containing a known pressure; wherein the port is arranged to facilitate the connection of a canister so as to place the gas canister in fluid communication with the port.

Preferably the gas canister contains a compressed gas at known pressure.

Preferably the gas canister is a disposable single use gas canister comprising a seal, the seal being adapted to be ruptured so as to connect the gas canister with the port substantially without loss of pressure.

Preferably the blood pressure monitor includes an inflatable cuff which is arranged in use around a part of the user's body, and the pressure sensing means is arranged to sense the pressure of gas within the cuff.

The apparatus may be arranged to rupture a seal of the canister only after the adapter is connected to the port, for example, by providing the rupturing means on the port, and by providing the canister with an engagement portion that is engageable in fluidly sealed manner with the adapter but not with the port, whereby the adapter is engageable in an engaged position in fluidly sealed manner with the port, and in the engaged position the rupturing means is arranged to pierce the seal of the canister. Alternatively, a rupturing means may be provided on the adapter.

According to a further embodiment of the present invention, there is provided a blood pressure monitor including a shock sensor which records physical jolts, and an alerting means connected to the shock sensor that alerts a user to indicate that calibration is required when a sufficiently large mechanical shock, or series of shocks, have been recorded.

According to a further embodiment of the present invention, there is provided a blood pressure monitor including a timing means, and an alerting means connected to the timing means that alerts a user to indicate that calibration is required after a predetermined time period has elapsed.

According to a further embodiment of the present invention, there is provided a blood pressure monitor including display or output means that displays or outputs a blood pressure reading together with an indication of a calibration status of the blood pressure monitor.

According to a further embodiment, there is provided a blood pressure monitor including a pressure sensing means, a temperature sensing means, and a processor means, wherein the pressure sensing means is arranged to provide a pressure signal to the processor means, and the processor means is arranged to process the pressure signal to provide a pressure reading; and the temperature sensing means is arranged to provide a temperature signal to the processor means, and the processor means is arranged to adjust the pressure reading to compensate for the sensed temperature.

An illustrative embodiment of the present invention will now be described, purely by way of example and without limitation to the scope of the claims, and with reference to the drawings, in which:

Figure 1:
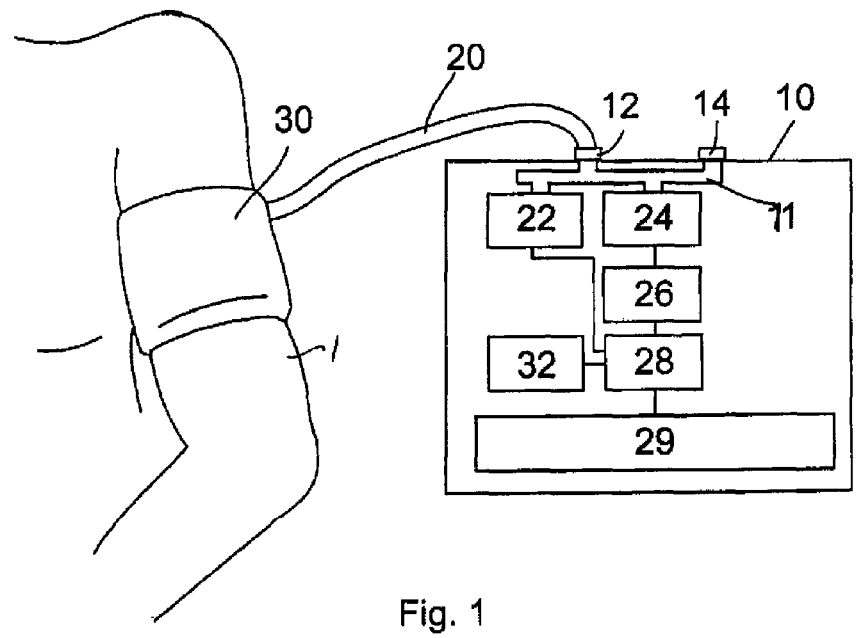
FIG. 1 is a diagrammatic representation of a blood pressure monitor.

Referring to FIG. 1, a sphygmomanometer or blood pressure monitor 10 is usually used in conjunction with an inflatable cuff 30, which is attached to the monitor 10 by a flexible tube 20. The tube 20 is connected to the monitor 10 by an attachment valve 12, which leads to a channel 11 which allows fluid communication between the tube 20 and a pump 22 and pressure sensor 24. The output of the pressure sensor is fed into an analogue to digital converter 26, and the resulting digital signal is transmitted to a processor (CPU) 28. The CPU 28 controls a display 29. The CPU 28 also controls the operation of the pump 22. In use, the inflatable cuff is attached to a patient's arm 1, and the user initiates the monitoring using an input 32, such as a keypad or touch sensitive display, which may be part of the display 29. The pump supplies compressed air which increases the pressure in the tube 20 and cuff 30, while the pressure sensor 24 monitors the pressure. The cuff is usually inflated to sufficient pressure to stop the arterial flow in the patient's arm, and then the pressure in the cuff is released over a time period, during which the arterial flow resumes, and then flows unimpeded. From the resumption of the arterial flow to unimpeded flow, the pumping action of the heart causes small oscillatory variations in the cuff pressure. By detecting these small oscillations above and below the average pressure by means of the pressure sensor 24, the CPU can determine when the systolic and diastolic pressures occur, and therefore, by calculating the underlying average pressure (i.e. removing the oscillatory variation) determine the systolic and diastolic pressures themselves.

The accuracy of the calculated systolic and diastolic pressures is dependent on the accuracy of pressure measurement by the pressure sensor 24. In order to calibrate the pressure sensor, accurately known static air pressure may be applied in accordance with known art, so that the output of the pressure sensor can be checked. This is usually repeated for a series of values over the required range of sensitivity. If there is a difference between the known static air pressure and the reading of the pressure sensor, the pressure sensor and/or the processor or other components of the apparatus can be adjusted as necessary until the monitor accurately reflects the applied pressures. This may be done for example by using the CPU to electronically adjust the pressure sensor, for example, by adjust the gain or other parameters of the internal amplifier of the pressure sensor.

This is usually carried out during the manufacturing process. However, over time, the accuracy of the pressure sensor decreases. This can be due to physical damage and knocks, the monitor's environment, or simply use. After a period of time therefore, the blood pressure monitor must be either replaced, or recalibrated. Conventionally, recalibration is carried out in a similar manner to the original calibration during manufacture. The blood pressure monitor must be attached (say at locking valve 14) to an air compressor which generates a series of known static air pressures with high accuracy. The pressure sensor's readings can then be compared with the expected values and the pressure sensor adjusted if necessary. As previously mentioned, this is inconvenient, because such an air compressor is an expensive and specialised piece of equipment, and usually requires the blood pressure monitor to be sent back to a factory to be recalibrated.

Figure 2:
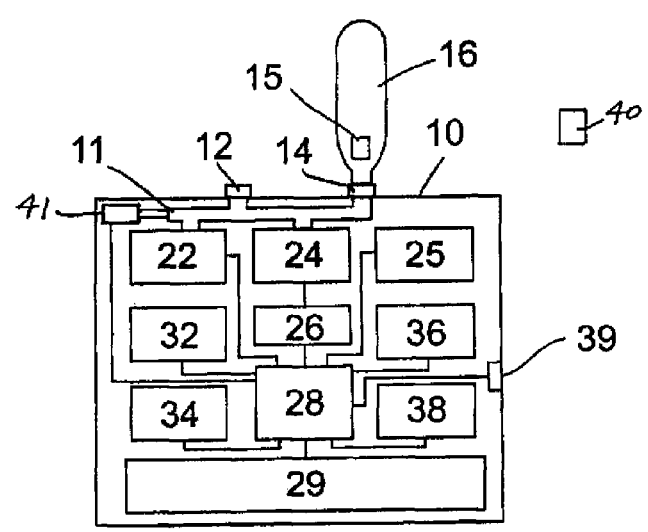
FIG. 2 is a diagrammatic representation of a calibration method and system comprising the blood pressure monitor of FIG. 1 and a disposable canister.

Referring to FIG. 2, a new method of recalibration is shown in relation to the blood pressure monitor 10. A gas canister 16 is provided, containing a volume of air at a known pressure. The blood pressure monitor is put into calibration mode, the cuff 30 and tube 20 are disconnected and a locking nut of the attachment valve 12 is closed. The gas canister 16 is attached to the blood pressure monitor at the locking valve 14, so that it is in fluid communication with the pressure sensor. The gas canister 16 and the locking valve preferably have a co-operating thread, and the locking valve includes a puncture means, so that the gas canister can be screwed onto the locking valve so as to accomplish a fluid tight seal, and the cap of the gas canister is perforated at the same time by the puncture means without causing loss of pressure to ambient.

When the gas canister 16 is perforated, the pressurised air from the gas canister is released into the channel 11. The volume of the channel 11 may be small relative to the volume of the gas canister, so that the pressure at the pressure sensor 24 is extremely close to the pressure of the gas in the gas canister. Alternatively, the volume of the channel can be taken into account when calibrating the pressure sensor and an allowance made for a known reduction in pressure caused by the expansion of the gas into the volume of the channel.

As well as allowing for the volume of the channel when calibrating the pressure sensor, the blood pressure monitor may include a thermistor or other temperature measuring sensor. The actual pressure, which will vary with temperature, may then be calculated using this temperature reading by the CPU, and therefore the calibration of the pressure sensor may be further improved. It should be noted that it is also advantageous to provide a temperature sensor in a blood pressure monitor independently of the calibration method, so that blood pressure readings may be adjusted to account for the ambient temperature.

The release of the gas from the gas canister into the channel may also result in a temperature change of the gas, which will be dependent on the pressure, the relative volumes of the canister and channel, and possibly on the type of gas employed. Although the method outlined above will allow a sufficiently accurate calibration, if desired, a thermistor or other temperature measuring sensor 41 may be included in the channel to compensate for the pressure variation due to temperature, or alternatively the monitor could be allowed to reach a temperature equilibrium with the room in which it is used.

While in calibration mode, the CPU of the blood pressure monitor records the constant pressure read by the pressure sensor, and compares this with the expected pressure provided by the gas canister. The expected pressure could be input by the user, but is more conveniently pre-programmed in the CPU, so that the user simply has to input an identifier (ID) printed on the gas canister, which could be for example a numeral or letter, which is also stored in a memory 36 in association with the value of the pressure of the canister. The stored values and identifiers may be downloaded periodically from a remote database via a USB connection 39. Even more conveniently, the blood pressure monitor includes a radio frequency receiver 25 and the gas canister includes an identifier such as a radio frequency identification (RFID) tag 15. The radio frequency receiver 25 detects and identifies the gas canister when it is in sufficiently close proximity (e.g. when it is connected to the monitor), and transmits this to the CPU, which then looks up in memory 36 the stored value of the calibration pressure within the canister.

After use, the gas canister is disposed of. Advantageously, the canister is a disposable single use canister. Since it is not re-usable, each canister thus provides an accurately predetermined stored calibration pressure so that each instance of calibration is carried out with a new canister which has been filled and sealed in a controlled factory environment.

As in the case of the known calibration technique carried out by the manufacturer, the method shown in FIG. 2 ideally includes calibration by applying several known pressures to the pressure sensor. Several gas canisters at different precisely known pressures are provided, and each attached in turn to the blood pressure monitor to check the accuracy of the pressure sensor through a range of pressures. If an RF receiver and RFID tags on the gas canisters are employed, the expected pressure for each reading is supplied by the RF receiver to the CPU.

After the required pressures have been applied to the pressure sensor, the CPU can automatically recalibrate the input received from the pressure sensor so that the blood pressure monitor is correctly calibrated.

As well as or instead of using a dedicated locking valve 14 on the blood pressure monitor, a gas canister could be attached utilising the valve 12 to which the tube 20 to the cuff 30 is attached, or indeed any suitable existing port or air jack in fluid communication with the pressure sensor. An adapter 40 could be used to connect the gas canister and such a port, and the adapter could also include a perforation means to release the pressurised gas.

Gas from the canister could also be released by establishing a sealed fluid connection to the port in the monitor using some other means than perforation, such as a valve or catch means provided on the top of the canister which can be opened slightly before, during, or after the canister is fully mechanically attached to the blood pressure monitor, either automatically as part of the fitting process, or by operation by the user.

The blood pressure monitor may include a timing means comprising a clock 38, and non-volatile memory 36 which can be written to. Where this is provided, the blood pressure monitor can record the date and time when a calibration procedure has been carried out (and if required what gas canisters were used), and also alert the user when a predetermined time period has elapsed since the last calibration procedure that another calibration should be carried out.

Some blood pressure monitors now communicate (using the internet or other wide area networks) with health services providers for automatic home monitoring, for example, via a USB port 39. Where this is done, the calibration status of the blood pressure monitor can also be communicated, so that the health services providers can place more confidence in remotely provided readings.

The blood pressure monitor may also be provided with an accelerometer or other shock sensor 34 that can sense and record in memory 36 when the blood pressure monitor has been subjected to a shock or jolt; and alerting means (e.g. software incorporated into the CPU) responsive to the shock sensor, whereby when a sufficiently large mechanical shock, or series of shocks have occurred, the CPU 28 of the blood pressure monitor can alert the user (and/or remote monitoring personnel) to indicate (via display 29, USB connection 39, or otherwise) that a calibration is necessary. It should be noted that it is also advantageous to provide a shock sensor in a blood pressure monitor independently of the above described method, so that a user can be informed that it is necessary to have the blood pressure monitor calibrated by conventional calibration means, or to replace the blood pressure monitor.

RFID tags generally include a unique identifier code. This may be used to check the status of each gas canister. For example, if the blood pressure monitor is in communication with a health service provider, a remote central database may be checked to ensure that the gas canister being used in the calibration process has not been previously used or that its useful lifetime has not expired.

It will be realised that this method may also be applied to the calibration of many different types of blood pressure monitor, including manually calibrated blood pressure monitors (and mechanical blood pressure monitors), and for blood pressure monitors supplied with a hand-operated bulb pump.

The invention is particularly advantageous in ensuring accurate calibration of blood pressure monitors of the type comprising an inflatable cuff, and in particular those suitable for monitoring the user's own blood pressure at home. It may also be used for blood pressure monitors which do not comprise an inflatable cuff, for example, those adapted for connection via a catheter to the patient's blood vessel, in which case the adapter may provide a fluid column and/or a membrane that provides a fluid barrier to transmit pressure between the canister and the monitor.

The canister 16 may comprise a closed vessel of any convenient type, such as a cylinder, vial, ampoule, cartridge, or the like, made for example from metal, glass or plastics material and comprising a connection portion adapted to provide both mechanical and sealing fluid connection to the port of the monitor. The mechanical connection can comprise a screw thread, flange, or any other suitable means, and the fluid seal can be integral with the mechanical connection or can include a surface, gasket, resilient seal, or other element adapted to provide a pressure tight sealed fluid connection to the monitor when the canister is mechanically connected thereto. The canister may provide a frangible seal such as a thin metal or plastics membrane adapted to be pierced by a penetration means or piercing element of the monitor after connection thereto. Preferably the seal is arranged such that the canister may not be refilled.

The port may be arranged to facilitate the releasable connection of the cuff to the port, in which case the cuff may be connectable directly to the port or via an adapter which is connectable to the port. The port may be adapted for connection of the canister directly thereto. Alternatively, the port may be adapted for connection of an adapter to the port, the adapter being adapted for connection of the canister to the adapter so as to place the canister in fluid communication with the port.

The valve 14 or other port adapted to receive the canister may be connected with the cuff by suitable valve means, whereby when the canister is connected to the valve 14, the cuff is exhausted and/or the valve 12 is closed and/or the valve 14 is isolated from any pressure within the cuff. The valve means may be automatically operable by connection of the canister to the port, or may preclude the connection of the canister to the port unless the valve means are first operated to exhaust or isolate the cuff.

The pressure sensor may comprise a diaphragm with one side in fluid communication with the port, and the other side connected to a pressure transducer. In alternative embodiments, rather than applying a positive pressure to a front side of a diaphragm forming part of the pressure sensor which in use experiences the positive pressure within the cuff, the novel canister might contain a gas at a negative (relative to ambient) pressure, i.e. a partial vacuum, or alternatively may be completely evacuated, and the port may be adapted to apply that negative pressure to a reverse side of the diaphragm whose front side in use experiences the positive pressure within the cuff; whereby the port for calibration need not be fluidly connected to the port which communicates with the cuff in use. In such embodiments, valve means may be arranged to exhaust the cuff when the canister is connected to the port, the valve means preferably being operated automatically by connection of the canister to the port. In such embodiments, references hereinbefore to a "gas" are construed mutatis mutandis as including a gas at low pressure relative to ambient, and including a vacuum defined by the substantial or complete absence of gas.

It will be understood therefore that the known pressure contained in the canister is gaseous pressure, which may be the stored pressure of a gas or the negative gauge pressure of a vacuum.

In yet further alternative embodiments, rather than connecting the canister in fluid communication with the diaphragm or other element of the fluid sensor that communicates with the cuff in use, it may be connected in fluid communication with a separate diaphragm, or a discrete portion of the diaphragm that communicates with the cuff in use, which separate diaphragm or portion may be for example relatively smaller than that which receives the gaseous pressure of the cuff, so that the gaseous pressure in the cylinder may conveniently be relatively higher than that applied in use to the cuff.

In yet further embodiments, channel 11 could provide a relatively large, known volume whereby the canister 16 may contain a relatively small volume of (preferably dry) gas at relatively high pressure which expands substantially when released into the channel, and the pressure applied to the pressure sensor is lower than of the stored gas in the canister such that the size of the canister may be conveniently reduced. A temperature sensor 41 may be provided, whereby the pressure sensing means 24 is arranged to provide a pressure signal to the processor means 28, and the processor means is arranged to process the pressure signal to provide a pressure reading; and the temperature sensing means 41 is arranged to provide a temperature signal to the processor means, and the processor means is arranged to adjust the pressure reading to compensate for the sensed temperature. Alternatively, the temperature sensor may delay the pressure reading until the temperature has risen to a predetermined temperature.

It will be understood that to apply the known pressure within the canister to the pressure sensor is construed to include to apply the known pressure as modified by expansion of gas within the canister to the pressure sensor so as to obtain a known modified pressure (the expected pressure).

In yet further embodiments, stored gas may be used in addition to or instead of the pump 22 to inflate the cuff. The diastolic and systolic pressures may be calculated as described above or otherwise in accordance with conventional art. Rather than RFID tags, contact ID tags or any other identification means may be used.

In yet further embodiments, two or more canisters or compartments within a canister may be connected to respective ports simultaneously so as to supply different known pressures simultaneously to different elements of the pressure sensor, whereby the pressure sensor may provide a reading reflecting a differential pressure, e.g. to compensate for ambient pressure.

In summary, in a preferred embodiment, a blood pressure monitor, particularly of the type having an inflatable cuff communicating with a pressure sensor and suitable for home use, may be calibrated by applying a sealed canister containing gas at a known pressure to a port so as to apply the known pressure to the pressure sensor, and comparing a pressure signal from the pressure sensor with the known pressure so as to determine a calibration error of the sensor and/or adjust the calibration of the sensor, e.g. by electronically adjusting the sensor. Several canisters may be used to calibrate the sensor across a range of pressures, each canister having a different known pressure. Each canister is preferably ruptured when attached to the port and is not re-usable, and may comprise an identifier such as an electronically readable identifier which is stored in a memory in association with the value of the known pressure within the canister. Temperature sensing means may be provided whereby the pressure reading is adjusted to compensate for temperature, e.g. of the gas released from the canister. The monitor may comprise means for sensing mechanical shock and alerting a user or remote monitoring personnel to provide an indication that recalibration is required.

Many other adaptations will be evident to those skilled in the art from the foregoing description, and it is to be understood that the scope of the invention is limited only by the claims.

The invention claimed is:

1. A method for checking or adjusting the calibration of a blood pressure monitor, the blood pressure monitor including a pressure sensing means, comprising the steps of providing at least one disposable, single use sealed canister, the canister containing a known, predetermined, stored pressure, connecting the canister in fluid communication with the pressure sensing means so as to apply the known pressure to the pressure sensing means, obtaining a reading from the pressure sensing means while the canister is in fluid communication therewith, and comparing the reading obtained from the pressure sensing means with an expected reading so as to check or calibrate the blood pressure monitor; wherein each instance of calibration is carried out with a new said disposable, single use sealed canister.

2. A method according to claim 1, wherein a plurality of disposable, single use sealed canisters filled with gas at different known pressures are connected sequentially in fluid communication with the pressure sensing means so as to check or calibrate the blood pressure monitor.

3. A method according to claim 1, wherein the or each canister is provided with a respective identifier, and the known pressure is associated as a stored value with the identifier; and the blood pressure monitor is provided with means for reading or inputting the identifier, and after reading or inputting the identifier of the respective canister, the blood pressure monitor retrieves the stored value associated therewith so as to determine the known pressure within the canister.

4. A method according to claim 1, wherein the blood pressure monitor is arranged to record physical jolts and to alert a user when calibration is required.

5. A method according to claim 1, wherein the blood pressure monitor includes display or output means that displays or outputs a blood pressure reading together with an indication of a calibration status of the blood pressure monitor.

6. A method according to claim 5, wherein the blood pressure reading and the indication are transmitted to a remote location.

7. A method according to claim 1, wherein the blood pressure monitor includes a temperature sensor, and for each instance of calibration, the blood pressure monitor is arranged to compensate for temperature using a sensed temperature reading from the temperature sensor.

8. A system comprising: a blood pressure monitor including a pressure sensor, a processor, and at least one port in fluid communication with the pressure sensor; and at least one disposable, single use, sealed canister, the sealed canister containing a known, predetermined, stored pressure; wherein the canister is directly or indirectly connectable with the port so as to place the canister in fluid communication with the port and apply the known pressure in the canister to the pressure sensor; the processor being arranged to compare a sensed value supplied by the pressure sensor with an expected value corresponding to the known pressure so as to check or calibrate the blood pressure monitor.

9. A system according to claim 8 wherein the canister is closed by a seal, and means are provided for rupturing the seal when the canister is connected in fluid communication with the port.

10. A system according to claim 8 wherein the or each canister is provided with a respective identifier, and the known pressure is associated as a stored value with the identifier; and the blood pressure monitor is provided with means for reading or inputting the identifier and retrieving the stored value associated therewith so as to determine the known pressure within the canister.

11. A system according to claim 8, wherein a plurality of said disposable, single use, sealed canisters contain different respective known pressures, and the processor is arranged to compare a sensed value supplied by the pressure sensor with a corresponding expected value, for each of said different known pressures when said plurality of canisters are connected sequentially in fluid communication with the port so as to check or calibrate the blood pressure monitor.

12. A system according to claim 8, wherein the blood pressure monitor is provided with a shock sensor for sensing physical jolts and alerting means responsive to the shock sensor for alerting a user when calibration is required.

13. A system according to claim 8, wherein there is included a display or output means that displays or outputs a blood pressure reading together with an indication of a calibration status of the blood pressure monitor.

14. A system according to claim 13, wherein the display or output means is arranged to transmit the blood pressure reading and the indication to a remote location.

15. A system according to claim 8, wherein the blood pressure monitor includes a temperature sensor, and for each instance of calibration, the blood pressure monitor is arranged to compensate for temperature using a sensed temperature reading from the temperature sensor.

16. A system according to claim 8, wherein the blood pressure monitor includes an inflatable cuff which is arranged in use around a part of a user's body, and the pressure sensing means is arranged to sense the pressure of gas within the cuff.

* * * * *